United States Patent [19]

Hill

[11] Patent Number: 5,065,615
[45] Date of Patent: Nov. 19, 1991

[54] PASSIVE ATMOSPHERIC LIQUID WATER MEASURING SYSTEM AND PROCESS

[76] Inventor: Geoffrey E. Hill, 2300 Canyon Blvd., Boulder, Colo. 80302

[21] Appl. No.: 490,173

[22] Filed: Mar. 8, 1990

[51] Int. Cl.$^5$ ............................................ G01W 1/00
[52] U.S. Cl. .................................... 73/29.01; 324/640
[58] Field of Search ........................... 73/29.01, 336.5; 324/640

[56] References Cited

U.S. PATENT DOCUMENTS

| | | | |
|---|---|---|---|
| 3,167,714 | 8/1962 | Seling | 374/22 |
| 3,380,055 | 1/1966 | Fow et al. | 374/122 X |
| 3,737,905 | 6/1973 | Haroules et al. | 342/351 |
| 3,911,435 | 10/1975 | Mardon et al. | 342/351 |
| 4,103,224 | 7/1978 | Taro et al. | 73/336.5 |
| 4,132,943 | 1/1979 | Gournay et al. | 324/337 X |
| 4,297,874 | 11/1981 | Sasaki | 73/73 |
| 4,385,516 | 5/1983 | Uffelman | 324/337 |
| 4,390,785 | 6/1983 | Faulhaber et al. | 250/330 |
| 4,441,363 | 4/1984 | Hill et al. | 73/170 R |
| 4,546,311 | 10/1985 | Knochel | 324/58.5 R |
| 4,716,360 | 12/1987 | Pakulis | 324/640 |
| 4,812,739 | 3/1989 | Swanson | 324/58.5 A |
| 4,820,970 | 4/1989 | Swanson | 324/58.5 A |

OTHER PUBLICATIONS

A Dual-Channel Microwave Radiometer for Measurement of Precipitable Water Vapor and Liquid, by Guirard, Howard & Hogg, IEEE Transactions of Geoscience Electronics, vol. GE-17, No. 4, Oct. 1979, pp. 129–136.

A Steerable Dual-Channel Microwave Radiometer for Measurement of Water Vapor & Liquid in the Troposphere, by Hogg, Guiraud, Snider, Decker & Westwater, Journal of Climate and Applied Meteorology, May 1983, vol. 22, pp. 789–806.

Automatic Digital Microwave Hygrometer, Model II, by Stokesberry & Hasegawa, The Review of Scientific Instruments, vol. 47, No. 5, pp. 556–558, May 1976.

Measurements and Interpretation of the Microwave Spectrum of the Terrestrial Atmosphere Near 1-Centimeter Wavelength, by Staeliln, Journal of Geophysical Research, vol. 71, No. 12, Jun. 15, 1966, pp. 2875–2882.

The Absorption of Microwaves by Oxygen by Van Vleck, Physical Review, vol. 71, No. 7, Apr. 1, 1947, pp. 413–424.

The Absorption of Microwaves by Uncondensed Water Vapor, by Van Vleck, Physical Review, vol. 71, No. 7, Apr. 1, 1947, pp. 425–433.

Primary Examiner—Jerry W. Myracle
Attorney, Agent, or Firm—Earl C. Hancock; F. A. Sirr

[57] ABSTRACT

The system is essentially an arrangement for determining the amount of liquid water in the atmosphere by monitoring the microwave signals received within a single frequency band around 31.65 GHz. The system has improved reliabililty since it is relatively simple employing existing technologies. It is generally a process and an arrangement wherein microwave signals naturally occurring in the atmosphere are detected by a receiver which is tuned to a relatively narrow band around the 31.65 GHz range. The converted signals from the microwave monitoring system are available for strip chart recording or for display directly or after introduction to a computer where they are processed by taking into account the known oxygen content of the atmosphere under monitor and the approximation of the vapor content. By recognizing these factors along with the cosmic radiation present, an output signal which is a close approximation of the actual liquid water content in the atmosphere is produced as a usable output signal for any utility device.

6 Claims, 3 Drawing Sheets

PASSIVE ATMOSPHERIC LIQUID WATER MEASURING SYSTEM AND PROCESS

BACKGROUND OF THE INVENTION

1. Field of the Invention

The present invention relates to devices and processes for determining the amount of liquid contained in the atmosphere at a given geographic location. More particularly, the present invention relates to apparatus and methods for employing radiometers to passively monitor the radiation received from the atmosphere and for transforming that radiation into data which indicates the amount of liquid water present in the atmosphere from which the detected radiation is emitted. The present invention is useful for weather research, weather forecasting and other monitoring applications.

2. Description of the Prior Art

Devices for determining the water content present in a given volume have typically employed an active transmitter and receiver combination in the past. For instance, U.S. Pat. Nos. 4,812,739 and 4,820,970 by Swanson show such a system for analyzing the water content of crude oil. Sasaki U.S. Pat. No. 4,297,874 determines the water content of sheet material by introducing it to a resonant cavity.

The Stokesberry and Hasegawa article entitled Automatic Digital Microwave Hygrometer, Model II in the May 1976 issue of the Review of Scientific Instruments at pages 556-558 suggests an arrangement for atmospheric humidity detection by introducing air into a captured environment of a resonant cavity.

Others have used active transmitters to survey the different gases present in a sample volume, sometimes using a single transmitter frequency as in U.S. Pat. No. 4,385,516 by Uffelman and others using swept frequencies as in U.S. Pat. No. 4,132,943 by Gournay et al. In Knochel U.S. Pat. No. 4,546,311, measurement of the moisture content of an aqueous solution is obtained by use of an active transmitter which provides a reference signal to an "evaluation arrangement" along with signals received by a probe in the solution.

Passive radiometer systems have found application for diverse measurement purposes. Methane gas is detected by Faulhaber et al U.S. Pat. No. 4,390,785 with an infrared radiometer and a system that splits received infrared signals to develop a reference signal. Seling U.S. Pat. No. 3,167,714 seeks to determine the absolute temperature of a body via a microwave radiometer operable around 35 GHz and a single antenna to sort thermally radiated signals from noise. Fow et al U.S. Pat. No. 3,380,055 sense temperature with a radiometer that varies the frequency pursuant to known absorption rates.

Dual frequency radiometer systems are shown in Haroules et al U.S. Pat. No. 3,737,905 and Mardon et al U.S. Pat. No. 3,911,435. Haroules et al is directed to solar radiation detection. Mardon et al is intended to discriminate between water, metal and other objects by converting the dual frequency signals received at an antenna and then comparing them to develop a difference frequency.

Recent systems for remote measurement of atmospheric vapor and liquid water employ dual frequency microwave radiometers. It is known that the two constituents of liquid and vapor, as well as oxygen, affect the intensity of microwave energy measured by the radiometers. Certainly when measuring vapor one must account for the presence of liquid as well as oxygen although the latter is merely a function of the surface pressure.

However, it has not been appreciated that when measuring liquid, the amount of vapor can readily be estimated by other simpler means along with oxygen as input for the liquid calculation. Because the vapor content of the atmosphere varies very much more slowly than does the liquid content, it is possible to use a single frequency for measuring liquid water. This is particularly true during winter when the vapor amounts are low to begin with.

DISCLOSURE OF THE INVENTION

The present invention is a system and process of atmospheric water measurement using a passive microwave monitoring configuration operating at a single frequency band in conjunction with a data processing device capable of correlating known factors with the detected information contained in the received single frequency. The output of this arrangement is an indication of the actual water content of the atmosphere monitored. Preferably the single frequency monitored is around 31.65 GHz. While there is a remote possibility that the present invention is applicable for a frequency selected from the range of about 10 GHz to 60 GHz, it is believed more practical to select the signal from a range of above 27 GHz and below 42 GHz.

By choosing a single frequency in accordance with this invention, many simplifications result with respect to the radiometer and it supporting structure and operation. These simplifications make it possible to avoid several difficulties in operating such a measuring device. In fact use of a single frequency system allows a return to a basic and thus more reliable configuration of a microwave radiometer. Thus an important feature of this invention is the use of a single frequency radiometer for the measurement of atmospheric liquid water.

The present invention is a system for determining the liquid content in the atmosphere above a given location. It employs a microwave radiometer including an antenna positioned to detect microwave signals emitted from the atmosphere above the given location with the radiometer operating substantially at a single frequency. The signals received at the radiometer are converted to an output signal having a magnitude correlated to the magnitude of the microwave signal received by the antenna. The converted signal magnitude is utilized for producing an output indicative of the liquid content of the atmosphere emitting the microwave signals and based upon predetermined quantities of other constituents in the atmosphere at the given location.

The system can include an arrangement for storing data reflecting a predetermined relationship of the magnitude of the converted output signals to an output indicative of the liquid content of the atmosphere based upon predetermined quantities of other constituents in the atmosphere at the given location. This makes it possible to compare the converted output signals with the data stored for producing an output indicative of the amount of liquid contained in the atmosphere from which the received microwave signals were emitted.

The single frequency received by the radiometer is preferably a frequency above the frequency wherein detectable liquid absorption occurs but below the frequency wherein oxygen absorption would prevent accurate liquid level determinations. Generally the microwave radiometer is set to receive substantially a single frequency within the range of about 27 GHz and 42 GHz. Other constituents for which compensation is incorporated into the stored data include vapor and oxygen as well as the small amount of background cosmic radiation. Best results to date have occurred with a single frequency of approximately 31.65 GHz. The process of determining the amount of liquid water present in the atmosphere above a geographic station is initiated with the steps of detecting the presence of naturally occurring microwave signals from a single frequency band where that signal was emitted from the atmosphere at the monitoring station. From this is produced an output signal reflecting the magnitude of the detected signals which occurred at a frequency above that at which detectable liquid absorption occurs but below that at which substantial oxygen absorption occurs. This output signal is used to determine the atmospheric liquid level compensated for the absorption of at least the vapor constituent within the atmosphere which emitted the microwave signals received.

The single frequency for this process is preferably selected from the range of about 27 GHz to 42 GHZ. The correlation processing step can include the step of compensating for oxygen and cosmic radiation from outer space in the atmosphere at the geographic station. The correlating step of the process can include the step of storing a table of received microwave signal magnitudes in correspondence to liquid content as a function of said predetermined constituents.

Another feature of this invention relates to the apparatus for monitoring the liquid content of the atmosphere at a geographic location which uses a radiometer including an antenna for receiving microwave signals from the atmosphere over the geographic location. This feature includes a housing for enclosing the radiometer and having a window transparent to microwave frequencies which the radiometer monitors. This window is located in intermediate relation between the antenna and the atmosphere overlying the geographic location. The housing also has associated therewith means for removing loose material such as snow, ice, rain, dust, debris, etc., from the external surface of said window.

The structure for removing loose material can include a structure for directing a jet of air across the outer window surface. A controller periodically actuates the air jet. Correlation of the output sampling from the radiometer with the periodic operation of the air jet actuator will ensure minimal discounting of the results obtained from intervening loose materials. Examples of structures for producing the air jet include air compressors coupled through an actuator controlled valve into a nozzle, blowers, or the like.

Those having normal skill in the art will recognize the foregoing and other objects, features, advantages and applications of the present invention from the following more detailed description of the preferred embodiments as illustrated in the accompanying drawings.

DETAILED DESCRIPTION OF THE PREFERRED EMBODIMENT

Figure 1:
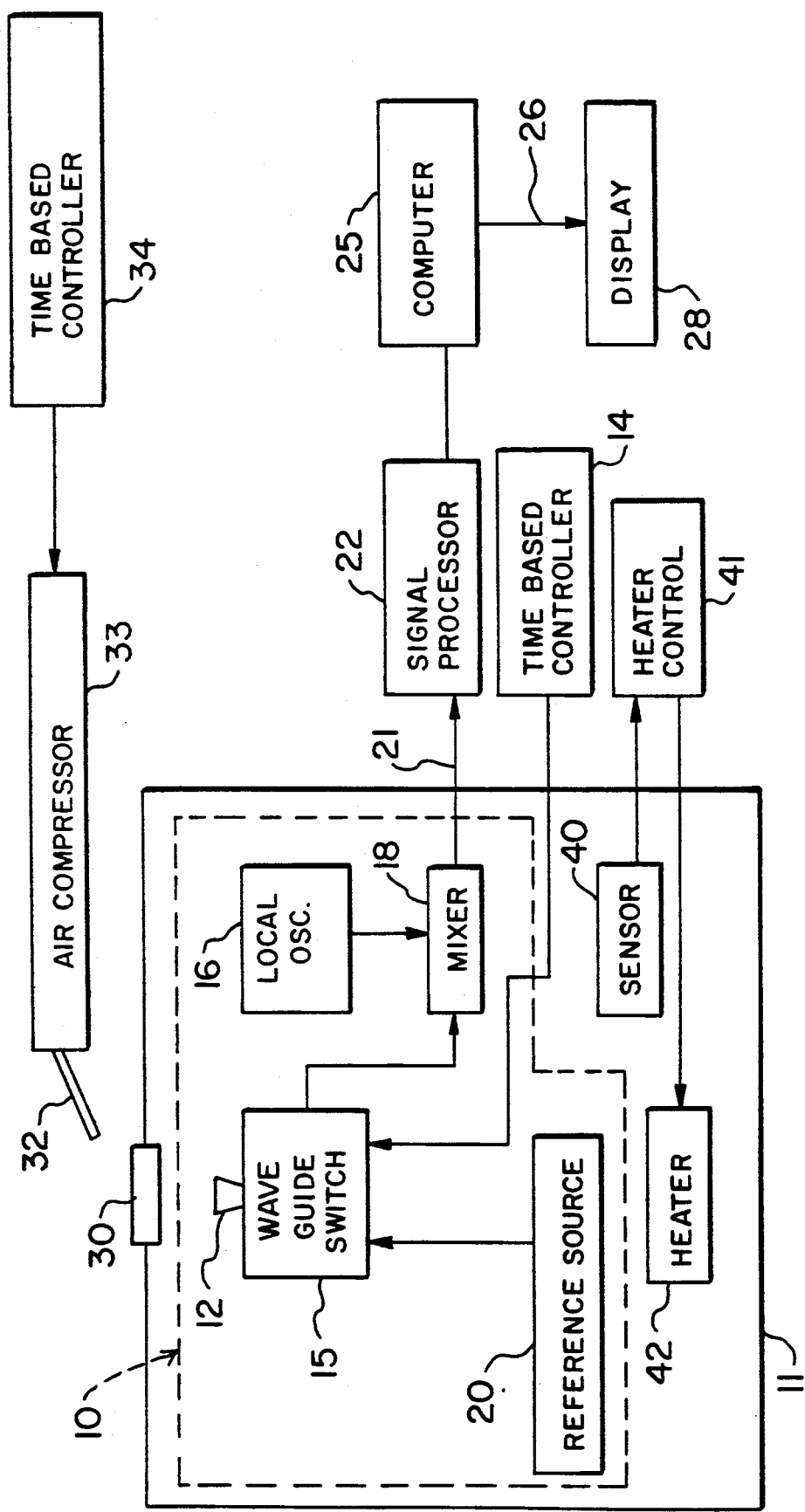
FIG. 1 is a system diagram of a radiometer and its supporting elements in accordance with this invention.

FIG. 1 is an overall block diagram of the components arranged for operation in accordance with one embodiment of this invention. The radiometer portion 10 of the system is contained within housing 11 and consists of microwave receiving components which are each contemporaneously available. The main elements are a horn antenna 12, a waveguide switch 15, a local oscillator 16, a mixer 18, and a reference source 20.

The radiometer itself is placed in a temperature controlled housing 11 which is typically mounted outside of a building or trailer. The horn antenna 12 of the radiometer views the sky through a small teflon or mylar covered window 30, which is kept clear of ice, snow and water by periodically blasting air from nozzle 32 of compressor 33 on the outer surface of window 30. This procedure is much more effective for the single frequency radiometer, because the area thus maintained is much smaller compared to the large reflector required for dual frequency radiometer.

The output 21 of radiometer 10 is introduced to a data processing system. It consists of a signal processor 22 which includes an analog to digital converter, and a computer 25. The computer 25 is enabled with suitable software which yields an output signal 26 corresponding to the atmospheric liquid water from the output 21 of radiometer 10. Output 26 is available for a variety of uses such as actuation of a display 28.

There are four functional electronic circuits or subsystems used to operate the radiometer 10. The first is waveguide switch controller 14 used for calibration by periodically switching reference source 20 through switch 15. The second is air compressor 33 with its time based on/off controller 34 used to clear ice, water or debris from the external surface of window 30 for horn antenna 12. A sensor 40 detects the temperature of the interior of housing 11 to provide an input to heater control 41 so as to appropriately actuate heater 42 to maintain a constant temperature for the environment of radiometer 10. Finally, signal processor circuit 22 conditions the output 21 of radiometer 10 for use by computer 25.

Control 14 for waveguide switch 15 and on/off control 34 for compressor 33 can use the same general circuit design except for specific component values. Clocks are used to determine the time span between actuations. A clock in controller 14 selects the intervals between waveguide switch 15 actuations for calibration purposes while a clock in controller 34 determines the time between blasts of air from nozzle 32 onto window 30. Timers are used for determining the duration of each actuation, one for waveguide output calibration and the other for occurrence and duration of air blasts. In an existing embodiment of this invention, the waveguide switch is calibrated every hour for thirty seconds while the compressor is turned on once every minute for approximately 0.4 seconds.

Heater controller 41 utilizes a comparator in which the variable input is from a voltage divider made with a resistance thermistor to ground and a potentiometer coupled to a power supply (e.g.: +12 volts). This input is compared with a reference input from another voltage divider made with two equal resistors, one to ground and the other to the power supply. With this design, the potentiometer is set to the resistance of the thermistor at a particular desired temperature. The output of the comparator goes high when the temperature falls below the desired value and causes a transistor to turn on a relay that passes current through heater 42 which is a resistance-wire heater or the like inside the radiometer enclosure 11. The heater 42 turns off when sensor 40 detects the temperature inside housing 11 exceeds the desired level.

The radiometer output signal 21 comes from a commercially available intermediate frequency (IF) mixer 18 which utilizes local oscillator 16 in producing output signal 21. The output is further processed by an operational amplifier in signal processor 22. The specific configuration of amplifier depends upon the use intended for its output. It can go to a display, strip chart or other recorder and/or pass for further processing by a computer 25. In the FIG. 1 embodiment, the signal is conditioned to pass through an analog to digital converter (ADC) in signal processor 22 whereupon the digital signal is introduced to computer 25 which handles it in accordance with the mathematical relationships discussed further below. The signal conditioning is done by use of offset and gain factors associated with the operational amplifier as is conventional.

While the liquid water amounts derived from either a single frequency system in accordance with this invention or a prior art dual frequency system may, or may not, yield true representations of liquid water content in the monitored atmosphere, the description below will show that the liquid water found from a single frequency radiometer will reproduce approximately those of a dual frequency system. Furthermore, the single frequency system will usually suffer fewer operational problems than the dual frequency system, because of the overall simplicity of the former.

The preferred frequency utilized by the single frequency radiometer is selected according to well known principles. Preferably the single frequency used is one of the two frequencies commonly used in a dual frequency radiometer.

Figure 2:
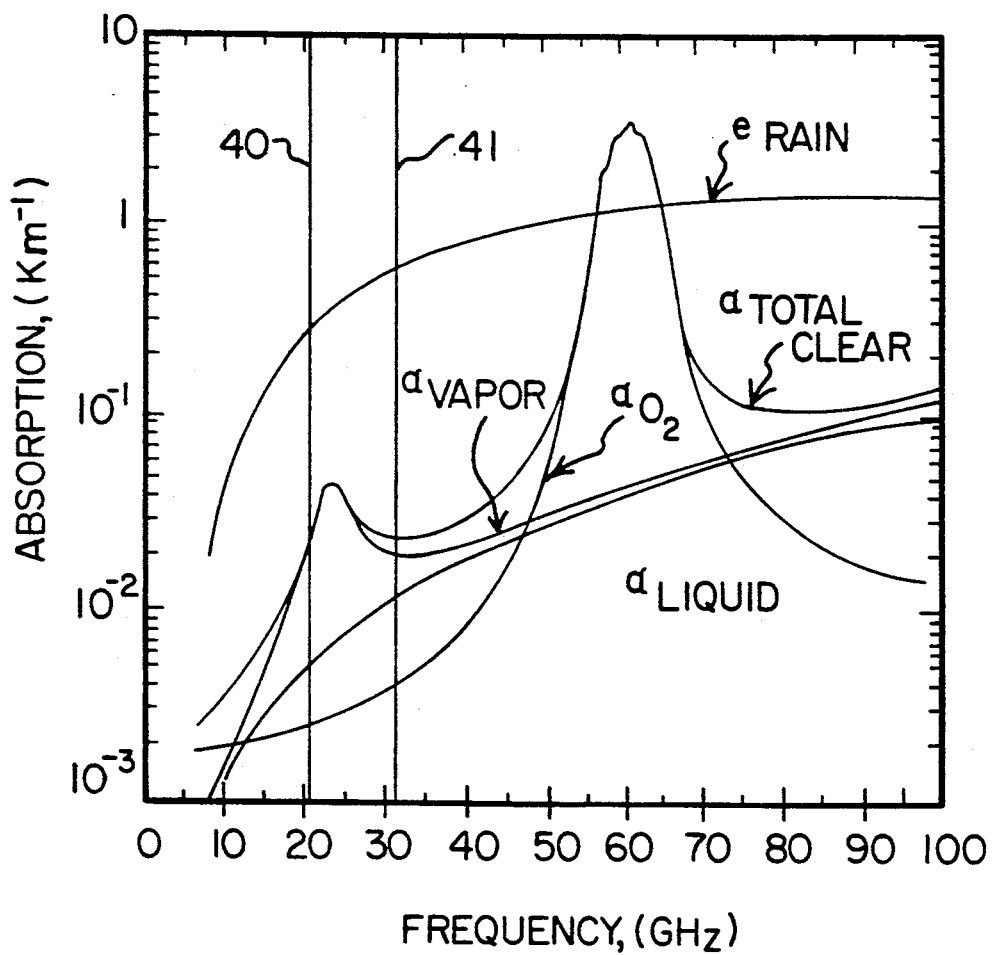
FIG. 2 is a graph of the atmospheric absorption characteristics of different constituents for a particular set of values as a function of frequencies in the microwave range.

FIG. 2 is a graph of the atmospheric absorption characteristics of different constituents for a particular set of values as a function of frequencies in the microwave range. This particular chart is for a temperature of 288.16 K, atmospheric pressure of 1013.25 mb, water vapor concentration of 7.5 g/m$^3$, liquid concentration of 0.1 g/m$^3$, and a rain rate of 12.5 mm/hr.

As is apparent from FIG. 2, the frequency of 31.65 GHz (noted by line 41) is affected substantially by liquid water, but is well below the strong oxygen line near 60 GHz and is at a relative minimum of vapor effects. A frequency of 31.65 GHz not only has the foregoing features but is a protected one as well. Other frequencies near the one selected are likewise considered suitable; frequencies between approximately 27 GHz and 42 GHz are considered particularly feasible. Note that as shown in FIG. 2 the frequencies from perhaps just above 25 GHz to around 50 GHz conceivably could prove satisfactory, although a frequency closer to the intermediate minimum in vapor absorption is preferred. The prior art two frequency systems used dual frequencies such as is indicated by lines 40 and 41.

The output signal 21 from the single frequency radiometer 10 is processed according to known theoretical relationships; oxygen and vapor effects are accounted for independently. The oxygen effect is accounted for according to the altitude of the station where the radiometer is located. The vapor effect is accounted for according to either a climatological estimate, or amounts based upon independently made measurements such as those made routinely by the National Weather Service. In particular, liquid water may be described by an equation:

$$L = -b_0 - b_1{}^*V + b_2{}^*T_B \qquad (1)$$

where * is the multiplication symbol, L is the total depth of atmospheric liquid (cm), V is the total depth of atmospheric vapor (cm) if it were converted from vapor to liquid, $T_B$ is the measured brightness temperature, and $b_0, b_1$ and $b_2$ are coefficients which depend upon the geographic location of the radiometer and upon the temperature of the liquid itself as is discussed below. As used herein, the term "brightness temperature" $T_B$ is defined by the expression $T_B = (1 - e^{-a}){}^*T_c$, where e = the natural number 2.71828, a = the absorption of the cloud in nepers, and $T_c$ = the average liquid temperature in the cloud.

The first term of equation (1) represents the main variation of the measurement due to liquid water, whereas the second and third terms are corrections for the presence of oxygen and vapor, respectively. The presence of cosmic background radiation is also included in the second term. Other equivalent forms of this equation are possible, such as one written in terms of absorption from the various constituents rather than in terms of brightness temperatures.

Figure 3:
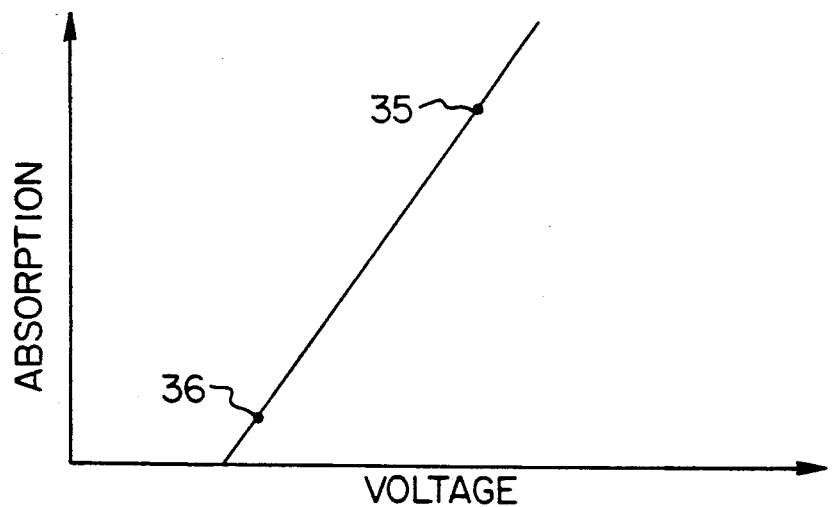
FIG. 3 is a plot of the voltage level output from a radiometer as correlated to the amount of atmospheric absorption of liquid water.

In FIG. 3 a graph of the relationship between the measured signal (a voltage) and brightness temperature is shown. Point 35 represents the values of brightness temperature and voltage found when the radiometer senses a reference source. It is entirely possible to use a second reference source maintained at a higher temperature to establish two reference values of voltage and corresponding brightness temperature. However, in the present configuration only one reference is used, but a second pair of values denoted on FIG. 3 by point 36 is found by measuring the voltage and corresponding brightness temperature when there is no liquid present, such as when the sky is clear.

The position of point 36 will vary slowly with time and by relatively small amounts in accordance with changes in total atmospheric vapor viewed by the horn antenna 12. Liquid water amounts are derived from the departures from Point 36 along the line connecting points 35 and 36.

The brightness temperature change due to liquid is found by measuring a change in voltage (V) of the radiometer output from its value when no liquid is present. That is, $$T_{B2} = T_{B2o} + (\Delta T / \Delta V)\delta V \qquad (2)$$

where $(\Delta T/\Delta V)$ is the slope of the line (e.g.: FIG. 3), $\delta V$ is the measured voltage change by the radiometer, and $T_{B2o}$ is the brightness temperature with no liquid present. The subscript 2 is used to denote channel 2 of a two frequency system which might operate at the 31.65 GHz frequency. The details of how equations (1) and (2) are utilized in a single frequency system as well as the basis for doing so are described in following sections.

There are many differences between the single frequency of the present invention and the contemporary two frequency system. In the two frequency system a highly specialized antenna is used. It consists of a computer-milled horn antenna, a computer-milled parabolic reflector, and a large flat reflector (0.6 m×0.9 m). These units mandate positioning in a specific orientation and require a substantial space. Also, during precipitation it is difficult to keep the flat reflector clear of ice and snow. In the single frequency system such as FIG. 1 hereof, the horn 12 views directly through a small window 30 from the interior of housing 11.

Prior art dual frequency systems require a frequency splitter because two frequencies are used. In the single frequency system hereof, no splitter is used. In the two frequency system, a microwave circulator is used (200 cps) to accommodate two reference sources for each frequency. High accuracy is needed because of the sensitive interrelation between data from the two frequencies. In the single frequency system of this invention, a simple wave guide switch 15 is used.

Because the prior art system uses two references as mentioned above, a total of four references are used, two of which are maintained at approximately 100° C. above the box or housing temperature to an accuracy of approximately 0.1° C. In the single frequency system of FIG. 1 hereof, only one reference source 20 is used and it is maintained at the temperature within the box or housing 11.

Furthermore, rather complicated electronics are used in the prior art two frequency system because all the data is handled synchronously from both channels. In the single frequency system, reference monitoring is done only every few minutes or longer, rather than 200 times per second as is necessary with a two channel system.

Elevation and azimuth scanning are much more difficult in the two frequency system because of the need to rotate the large reflector on two axes. Because the reflector is about two meters or so from the horn, the azimuthal rotation is particularly cumbersome. With the single frequency system the box 11 containing the radiometer 10 is rotated near the center of gravity, so only a much smaller mechanism is required.

The theoretical basis for using a single frequency instead of a dual frequency microwave radiometer is found by use of the equations governing absorption of microwave radiation. The brightness temperature equations for the two channels in accordance with Guiraud et al are:

$$V = 0.0190 + 0.11800 * T_{B1} - 0.05600 * T_{B2} \tag{3}$$

$$L = 0.018 - 0.000114 * T_{B1} + 0.00284 * T_{B2} \tag{4}$$

where $T_{B1}$ and $T_{B2}$ are the brightness temperatures in °K. at 20.6 and 31.65 GHz, respectively, V is the total vapor and L is the total liquid, both expressed as precipitable water in cm. The coefficients in these equations may differ slightly according to specific location and altitude. Those used here are for middle latitude western U.S. with a mean surface pressure of approximately 850 mb.

These equations are written in the brightness temperature form as $$T_{B1} = 5.70 + 10.46 * V + 206.3 * L \tag{5}$$

$$T_{B2} = 8.63 + 4.204 * V + 435.1 * L \tag{6}$$

An appropriate formulation for a single frequency microwave radiometer may be developed for that frequency, 31.65 GHz. The sources of information are similar to those already known. These sources include the work of Van Vleck, Goldstein and others. For liquid water droplets the formulation is that derived from Goldstein as given in Staelin. Here the formula is valid for droplets less than about 150 micro-meters when a frequency of 31.65 GHz is used. This is generally appropriate for cloud droplets, but not necessarily for rain.

The absorption (db) may be written as:

$$A = 43.43 * (L/\lambda * (10^{3.55 - T/82}) \tag{7}$$

where $\lambda$ is the wave length, L is the precipitable liquid (cm), and T is the cloud temperature (K°). Absorption and brightness temperature of the liquid by itself ($T_{B2}'$) are related by $$A = -4.343 * \ln((T - T_{B2}')/(T - 2.9)) = 4.343 * ((T_{B2}' - 2.9)/(T - 2.9)) \tag{8}$$

By combining the relation (7) for a frequency of 31.65 GHz with (8), a linearized result is $$T_{B2}' = (5131 - 17.05 * T) * L \tag{9}$$

and by replacing the last term in (6) by the right hand side of (9), the result is $$T_{B2}' = 8.63 + 4.204 * V + (5131 - 17.05 * T) * L \tag{10}$$

For a temperature of 275.4° K. the coefficient of L is the same as that from Guiraud et al, namely 435.1. With a temperature of 263° K., which is typical for supercooled liquid water, the coefficient of L is 646.9. The ratio of the two values is 1.487; that is for a given brightness temperature change there is only 1/1.487 or 0.673 times as much liquid by the new value compared to the amount by Guiraud et al. With such an important effect of temperature on the amount of liquid water present the formulation given by (10) is preferred over (6).

In accordance with either (10) or (6), a change in the brightness temperature of 2° K. at 31.65 GHz will occur by a change in vapor of approximately a half cm or by a change in liquid of 0.03 mm. During winter this change in vapor is within the range of a typical daily variation. On the other hand a change of 0.03 mm liquid is just above the minimum detectable amount. In other words ordinary changes in vapor during winter will have little effect on the measurement of liquid at 31.65 GHz. Furthermore, estimates of vapor can be made to reduce the already small effect of vapor changes. A more significant effect than vapor is due to changes in temperature of the liquid itself. For field applications (10) is written as $$L = (T_{B2} - 8.63 - 4.204 * V)/(5131 - 17.05 * T) \tag{11}$$

This equation is in a similar general form as given by equation (1). Here the vapor may be found independently as described below, $T_{B2}$ is measured as from equation (2) and the temperature of the liquid itself may be found from independent measurement or by a climatological value.

The measured value of $T_{B2}$ is actually found by first measuring a voltage output 21 from the radiometer 10. This output can be recorded on a strip chart or the output can be fed to an analog to digital converter in signal processor 22 and then into computer 25. The brightness temperature is then found in computer 25 by use of software implementation of equation (2).

To demonstrate the practical application of the foregoing analysis, consider actual data from a dual frequency microwave radiometer. These data were collected by the U.S. Bureau of Reclamation at Kingvale, Calif. during recent field seasons of the Sierra Cooperative Pilot Project (SCPP). The data utilized herein consists of two samples per hour (00 and 30 minutes past the hour) whenever the liquid was reported at greater than 0.49 mm at any time within the hour. In this way a wide range of liquid values are obtained.

Figure 4:
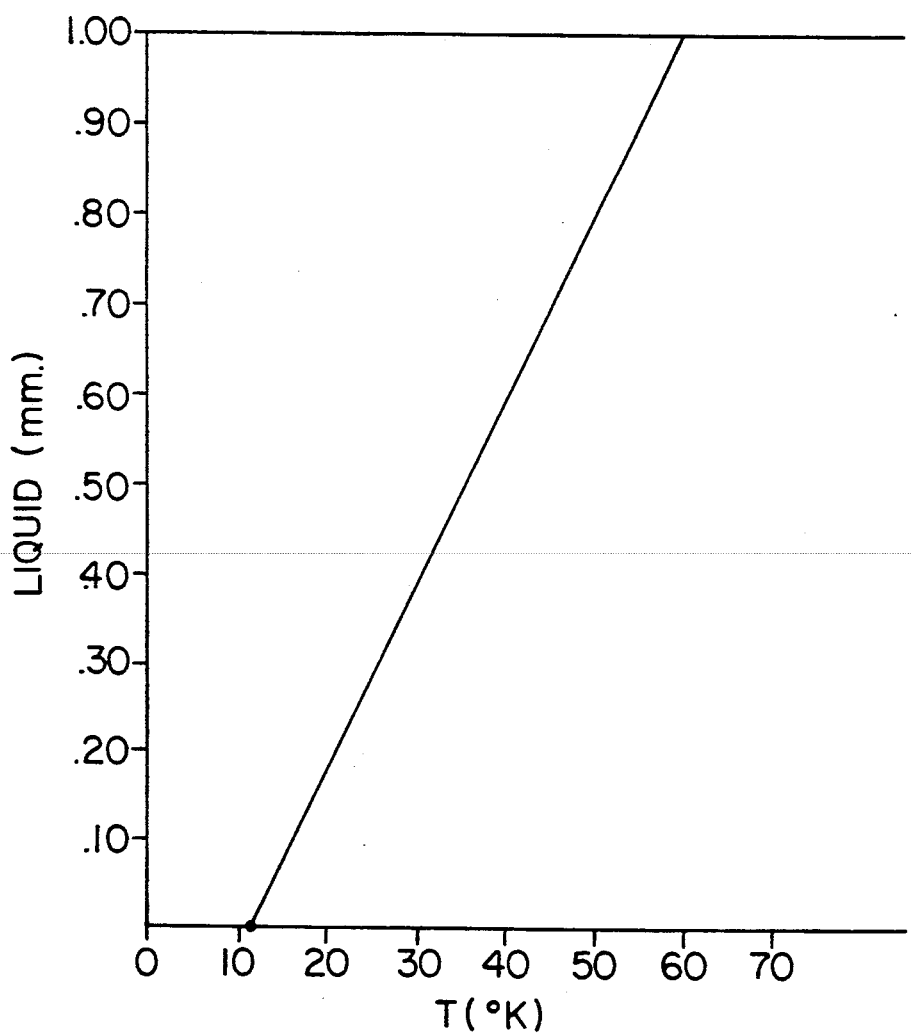
FIG. 4 is a plot of the amount of liquid content in the portion of the atmosphere monitored as a function of the brightness temperature detected for that monitored area.

Values of liquid (mm) are shown in FIG. 4 as a function of brightness temperature at 31.65 GHz for a two season period. It is clearly evident that during the winter months at a given location the brightness temperature at 31.65 GHZ accounts for nearly all of the change in liquid as measured without taking into account temperature variations. The range of liquid at a given brightness temperature is typically less than 0.05 mm. All of the detectable variation at a given brightness temperature is taken into account by including the vapor changes in accordance with equation (6).

For the use of a single frequency radiometer in accordance with this invention, there are several ways to reduce the effect of variations in vapor. First, it is recognized that vapor changes are much more gradual than liquid since the latter varies from zero to peak values as individual clouds pass over the radiometer. Therefore, use of a baseline value for liquid is one method. In fact even with the two frequency system, use is often made of a baseline value when there is obvious drifting of the zero value.

Second, a climatological value for vapor may be utilized. During winter especially at higher elevations, the departures from climatological values are small. Use of simple predictors such as surface temperature will further account for the effect of vapor changes. Third, measurements of vapor are usually available on a 12 hour basis by standard observations of precipitable water vapor. These measurements may be modified in space or time to appropriately correlate with the radiometer site. Fourth, vapor measurements from a nearby dual frequency radiometer may be utilized on a quasi-continuous basis to provide timely updates of vapor changes.

During the course of development of the single frequency system over several winters, the system was operated alongside of the dual frequency system of Utah State University. For liquid water measurements, the single and dual frequency systems yielded virtually the same result. This result is verified using data from the U.S. Bureau of Reclamation.

The major differences between the single and dual frequency systems appear when the radiometer reflector of the dual frequency system is covered with wet or melting snow, or water. With the single frequency system the window for the horn antenna is very much smaller than that of the dual frequency system. As shown in FIG. 1, window 30 is cleared by air from nozzle 32 of air compressor 33. At time intervals such as one minute, a blast of air is forced from nozzle 32 over the window which is typically about 8 cm × 10 cm. This action completely removes any snow or water so that at the moment after the blast the radiometer reading applies to a measurement of atmospheric radiation above the window surface. Subsequently, the measured brightness temperature may increase rapidly if it is raining or if wet snow is accumulating. When the next blast of air comes on, the measured value takes a sharp drop to the clear window value. Thus the occurrence of precipitation is evident, yet the minimum values yield the atmospheric reading.

The single frequency radiometer is directed toward any desired azimuth or elevation by a computer controlled positioning system not shown. From a mechanical standpoint this system is relatively simple because a typical radiometer housing 11 is small such as 22 cm × 22 cm × 40 cm. Several automatic scanning modes are utilized; one is an azimuth scan at a selected elevation; another is an elevation scan at a selected azimuth. A user friendly menu allows configuring of a variety of other scanning modes.

Analysis of the equations governing microwave measurements of vapor and liquid water show that while the liquid measurement may be needed for proper measurement of vapor, the reverse is not so. That is, the changes in vapor likely to occur (particularly in winter) have a small if not negligible effect on liquid. A means of taking into account the more important effect of temperature variations of the liquid itself is provided.

The construction and operation of a single frequency microwave radiometer is much simpler than that for a prior art dual frequency system. This simplicity applies to the microwave components, the supporting electronics, the antenna system, the ice/water clearing system, and the positioning system for azimuth and elevation scanning. All of these items contribute to achieving a reliable and cost effective measuring system.

Analysis of data collected by a dual frequency radiometer is used to demonstrate that a single frequency radiometer at 31.65 GHz can obtain liquid water measurements with a difference close to the minimum detectable amount of the dual frequency system. Furthermore, with the simplifying aspects of the mechanical and electronic components, there are frequent periods when the single frequency system provides more useful data than does the dual frequency system.

While the exemplary preferred embodiments of the present invention are described herein with particularity, those having normal skill in the art will recognize various changes, modifications, additions and applications other than those specifically mentioned herein without departing from the spirit of this invention.

What is claimed is:

1. A system for determining the liquid content in the atmosphere above a given location comprising:

a microwave radiometer including an antenna positioned to detect microwave signals emitted from the atmosphere above the given location with said radiometer operating at a substantially single frequency within the range of about 27 GHz to $\Delta$GHz, means for converting signals received at said radiometer to an output signal having a magnitude correlated to the magnitude of the microwave signal received by said antenna, and means utilizing said converted signal magnitude for producing an output indicative of the liquid content of the atmosphere emitting the microwave signals and based upon predetermined quantities of other constituents in the atmosphere above the given location, said utilizing means including, means for storing data reflecting a predetermined relationship of the magnitude of said converting means output signals to an output indicative of the liquid content of the atmosphere based upon predetermined quantities of other constituents including vapor and oxygen in the atmosphere above the given location, and means for comparing said converting means output signal with the data stored in said storing means for producing an output indicative of the amount of liquid contained in the atmosphere from which the received microwave signals were emitted.

2. A system in accordance with claim 1 wherein said substantially single frequency at which said radiometer operates is a frequency wherein detectable liquid absorption occurs but below the frequency wherein oxygen absorption would prevent accurate liquid content determinations.

3. A system in accordance with claim 1 wherein said substantially single frequency is approximately 31.65 GHz.

4. The process of determining the amount of liquid water present in the atmospheric area above a geographic station comprising the steps of;

detecting the presence of naturally occurring microwave signals from a single frequency in the range of about 27 GHz to 42 GHz which were emitted from the atmospheric area above the geographic station, producing an output signal reflecting the magnitude of said detected microwave signals which occurred at a frequency above that at which detectable liquid absorption occurs but below that at which substantial oxygen absorption occurs, and correlating said output signal to a liquid level compensated for the absorption of at least the vapor constituent within the atmospheric area through which the microwave signal passed, said correlating step including the step of compensating for oxygen and vapor constituents in the atmospheric area along with the cosmic radiation present at the geographic station.

5. The process in accordance with claim 4 wherein said correlating step includes the step of storing a table of received microwave signal magnitudes in correspondence to liquid content as a function of said constituents.

6. Apparatus for monitoring the liquid content of the atmosphere overlying a geographic location comprising a radiometer including an antenna for receiving microwave signals of a substantially single frequency within the range of about 27 GHz to 42 GHz from the atmosphere overlying said geographic location and further including means compensating said received signals for oxygen and vapor constituents in the atmospheric area along with the cosmic radiation present at the geographic location, housing means enclosing said radiometer and having a window therein located in intermediate relation between said antenna and the atmosphere overlying the geographic location, means including means for directing a jet of air across the external surface of said window for removing loose material from the external surface of said window, means for periodically actuating said jet air directing means, and means for correlating output sampling from said radiometer with operation of said periodically actuated means.

* * * * *